US005844121A

United States Patent [19]
Keller

[11] Patent Number: 5,844,121
[45] Date of Patent: Dec. 1, 1998

[54] METHOD OF INHIBITING MYCOTOXIN PRODUCTION IN SEED CROPS BY MODIFYING LIPOXYGENASE PATHWAY GENES

[75] Inventor: Nancy P. Keller, College Station, Tex.

[73] Assignee: The Texas A & M University System, College Station, Tex.

[21] Appl. No.: 582,339

[22] Filed: Jan. 19, 1996

[51] Int. Cl.$^6$ .......................... C12N 15/00; C12N 15/29; C12N 15/82; A01H 4/00
[52] U.S. Cl. ...................... 800/205; 800/205; 536/23.6; 536/24.1; 435/172.3; 435/69.1; 435/419; 435/320.1
[58] Field of Search .......................... 800/205; 536/23.6, 536/24.1; 435/172.3, 69.1, 419, 320.1

[56] References Cited

U.S. PATENT DOCUMENTS 5,349,122   9/1994   Hain et al. .............................. 800/205

OTHER PUBLICATIONS

Naploi et al. Introduction of a chimeric chalcone synthase gene into petunia results in reversible co–suppression of homologous genes in trans. The Plant Cell, vol. 2, 2769–289, 1990.

Doehlert et al. Evidence implicationg the lipoxygenase pathway in providing resistance to soybeans against *apergillus flavus*. Phytopathology, vol. 83, No. 12, 1473–1477, 1993.

Bell et al. Lipoxygenase gene expression is modulated in plants by water deficit, wounding and methyl jasmonate. Mol. Gen. Genet. (1991) 230: 456–462.

Gardner. Recent investigations into the lipoxygenase pathway of plants. Biochimica et Biophysica Acta. 1084 (1991) 221–239.

Burow G.B., Nesbitt, T.C., Dunlap, J.D., and Keller, N.P. (1997) Seed lipoxygenase products modulate Aspergillus mycotoxin biosynthesis. Mol. Plant Microbe Inter 10:380–387.

Burow, G.B., Gardner, H.W. and Keller, N.P. (1997) Phytopathology 87, S14.

Burow, G., et al., "Seed Lipoxygenase Products Modulate Aspergillus Mycotoxin Biosynthesis", *Molecular Plant–Microbe Interactions*, vol. 10, No. 3, 1997, pp.380–387.

Croft, K. et al., "Volatile Products of the Lipoxygenase Pathway Evolved from *Phaseolus Vulgaris* (L.) Leaves Inoculated with *Pseudomonas Syringae* PV Phaseolicola", *Plant Physiology*, vol. 101, 1993, pp. 13–24.

Derwent Publications Ltd., London, GB; *Database WPI*, Section Ch, Week 9219.

Gardner, H., "Biological Roles and Biochemistry of the Lipoxygenase Pathway", *Hortscience*, vol. 30, No. 2, Apr. 1995, pp. 197–205.

Harms, K., et al., "Expression of a Flax Allene Oxide Synthase cDNA Leads to Increased Endogenous Jasmonic Acid (JA) Levels in Transgenic Potato Plants But Not to a Corresponding Activation of JA–Responding Genes", *The Plant Cell*, vol. 7, No. 10, Oct. 1995, pp.1645–1654.

Peng, Y.–L., et al., "A Novel Lipoxygenase from Rice", vol. 269, No. 5, 4 Feb. 1994, pp. 3755–3761.

Zeringue, H., et al., "Relationships Between C6–C12 Alkanal and Alkenal Volatile Contents and Resistance of Maize Genotypes to *Aspergillus Flavus* and Aflatoxin Production", *Journal of Agricultural and Food Chemistry*, vol., 44, No. 2, Feb. 1996, pp. 403–407.

Jeffrey A. Anderson, "Lipid Peroxidation and Plant Tissue Disorders: Introduction to the Workshop," *HortScience*, vol. 30(2) (Apr. 1995) pp. 196–205.

D. W. Brown et al., "Twenty–five coregulated transcripts define a sterigmatocystin gene cluster in *Aspergillus nidulans*," *Proc. Natl. Acad. Sci. U.S.A.*, vol. 93,(1996) pp. 1418–1422.

G.B. Burow, et al., "Inhibitory Effects of Soybean Lipid Metabolites on Aflatoxin and Sterigmatocystin Biosyntheses in Aspergillus spp.", *American Peanut Research and Education society Proceedings*, Jul. 1995.

R. Butchko, et al., "Polyketide Biosynthesis in Aspergillus spp. as a Developmental Response to Lipid Substrate and Stress", *American Peanut Research and Education Society Proceedings*, 1993.

Marta Goodrich–Tanrikulu et al., "The plant growth regulator methyl jasmonate inhibits aflatoxin produced by *Aspergillus flavus*," *Microbiology*, vol. 141 (1995) pp. 2831–2837.

Nancy P. Keller, "Polyketide Biosynthesis in Aspergillus spp. as a Developmental Response to Lipid Substrata", *17th Fungal Genetics Conference*, Mar. 1993.

Nancy P. Keller, et al., "*Aspergillus nidulans verA* Is Required for Production of the Mycotoxin Sterigmatocystin", *Applied and Environmental Microbiology*, vol. 60, No. 5, May 1994, pp. 1444–1450.

Nancy P. Keller, et al., "A Visual Pattern of Mycotoxin Production in Maize Kernals by Aspergillus spp.", *Phytopathology*, vol. 84, No. 5, 1994, pp.483–488.

(List continued on next page.)

*Primary Examiner*—Douglas W. Robinson
*Assistant Examiner*—Thomas Haas
*Attorney, Agent, or Firm*—Fulbright & Jaworski LLP

[57] ABSTRACT

A method of inhibiting the production of mycotoxins of fungus, such as aflatoxin-producing and sterigmatocystin-producing fungi, in plants susceptible to contamination by such mycotoxins consists of introducing into the susceptible plant a gene encoding for lipoxygenase pathway enzyme of the mycotoxin. Exemplary of the lipoxygenase pathway enzymes are soybean lipoxygenase, allene oxidase, hydroperoxide lyase and hydroperoxide dehydratase. The resulting transgenic plant demonstrates substantial resistance to mycotoxin contamination of such fungus. Plants which are substantially resistant to mycotoxin contamination of Aspergillus spp. are further obtained by incorporating into mycotoxin susceptible plant antisense genes for the 9-hydroperoxide fatty acid producing lipoxygenases.

9 Claims, No Drawings

OTHER PUBLICATIONS

Dr. Nancy P. Keller et al., "Inhibition of Aflatoxin Biosynthesis by Altering Lipoxcygenase Metabolism in Ssceptible Plants," Research Proposal Submitted to USDA–ARS Preharvest Control of Aflatoxin Jane Robens, pp. 1–18.

T. Kaye Peterman, et al., "Behavior of Lipoxygenase during Establishment, Senescence, Rejuvenation of Soybean Cotyledons", *Plant Physiol.*, vol. 78, 1985, pp. 690–695.

James N. Siedow, "Plant Lipoxygenase: Structure and Function", *Annu. Rev. Plant Physiol. Plant Mol. Biol.*, 1991, pp. 145–188.

Christopher D. Skory, et al., "Regulated Expression of the nor–1 and ver–1 Genes Associates with Aflatoxin Biosynthesis", *Applied and Environmental Microbiology*, vol. 59, No. 5, May 1993, pp. 1642–1646.

METHOD OF INHIBITING MYCOTOXIN PRODUCTION IN SEED CROPS BY MODIFYING LIPOXYGENASE PATHWAY GENES

SPECIFICATION

1. Field of the Invention

The invention is drawn to a method of eliminating or substantially reducing toxicity in seed crops caused by colonization of fungi which produce toxic fungal metabolites called mycotoxins. In particular, the invention relates to a method of eliminating or substantially reducing toxicity in seed crops caused by colonization of aflatoxin-producing or sterigmatocystin-producing fungi. Colonization by aflatoxin-producing or sterigmatocystin-producing fungi, such as Aspergillus spp., leads to contamination of food and feed crops by aflatoxin/sterigmatocystin.

In addition, the invention is drawn to novel genetically enhanced crops containing the "anti-fungus aflatoxin or sterigmatocystin" gene which masks the detrimental effects caused by aflatoxin and sterigmatocystin.

According to the invention, a mycotoxin-inhibiting agent within the lipoxygenase pathway is transferred by genetic engineering techniques to crops susceptible to the mycotoxin. In particular, the invention is drawn to the transfer of an inhibiting agent of aflatoxin or sterigmatocystin to such aflatoxin/sterigmatocystin susceptible crops as corn, peanuts, treenuts, cottonseed, etc. Alternatively, the genes encoding lipoxygenase may be modified in-situ to render a product which masks the detrimental effects caused by aflatoxin and sterigmatocystin. Still, the invention is drawn to a method of blocking the transcription of the 9-hydroperoxy producing lipoxygenase genes by anti-sense genes. Still further, the invention is drawn to the creation of an "anti-Aspergillus aflatoxin or sterigmatocystin" gene (e.g. by altering lipoxygenase pathway enzyme production) and its incorporation into aflatoxin/sterigmatocystin susceptible crops.

2. Background of the Invention

Aspergillus spp. are seed-deteriorating fungi known for their ability to produce mycotoxins in crops such as maize, peanuts, tree nuts, almonds, Brazil nuts, pistachios, melon, pumpkin, sunflower seeds and cottonseed. Typically the mycotoxins produced by Aspergillus spp. during colonization are aflatoxin and sterigmatocystin. Aflatoxin is normally produced by *A. flavus* and *A. parasiticus*. Sterigmatocystin is produced by several Aspergillus spp. including *A. nidulans* and *A. versicolor*.

Aflatoxins have several structural forms. For instance, *Aspergillus flavus* produces aflatoxin $B_1$ and aflatoxin $B_2$. *Aspergillus parasiticus*—the second of the two aflatoxin-producing fungi—produces, on the other hand, aflatoxin $G_1$ and aflatoxin $G_2$ as well as $B_1$ and $B_2$. Of these, aflatoxin $B_1$ is the most toxic and carcinogenic. (Sterigmatocystin is similar in toxicity and carcinogenicity to aflatoxin $B_1$.) It further is the most prevalent of the aflatoxins in contaminated feedstocks.

Aflatoxin and sterigmatocystin, end products of the same biosynthetic pathway, are both derived from polyketides which are bioreactive secondary metabolites that are synthesized like fatty acids. A lengthy biosynthetic pathway has been proposed: initial polyketide precursor→norsolorinic acid→averantin→averufanin→averufin→versiconal hemiacetal acetate→versicolorin B→versicolorin A→demethylsterigmatocystin→sterigmatocystin→O-methylsterigmatocystin→aflatoxin $B_1$.

Infection of crops by Aspergillus spp. is highly undesirable since aflatoxin and the related mycotoxin, sterigmatocystin, are human carcinogens. In developing countries where governments cannot afford to screen and destroy contaminated food, high liver cancer rates are associated with aflatoxin/sterigmatocystin contamination.

In certain years, environmental conditions heavily favor the production of aflatoxin as well as sterigmatocystin It is necessary to survey food products and feeds for such contamination. Contaminated supplies in the U.S. are typically destroyed though at times contaminated supplies can be treated. As might be expected, the surveillance and resulting expense associated with the sampling, decontaminating and/or destroying of food supplies represents a herculean task.

In an attempt to deal with the problem of aflatoxin/sterigmatocystin contamination of food supplies, regulatory agencies have imposed allowable limits. While European countries have typically imposed a 0 ppb limit, the United States currently has a 20 ppb limit for certain foods.

The ideal solution is to of course prevent the occurrence of aflatoxin/sterigmatocystin food and feed contamination. Traditional plant protection practices, such as through breeding, have been unsuccessful. Current studies have further included the placement of antifungal compounds into susceptible crops by generic engineering techniques. Transformation of peanuts, cotton and walnuts with a variety of antifungal agents such as lytic peptides, bacterial endochitinase, tobacco osmotin, and chitinase have been made. Cary, J. W. et al., *Construction of Transformation Vectors Expressing Resistance to A. flavus in Cotton* p. 16, Proceedings from the 7th Annual Aflatoxin Elim Workshop Meeting, St. Louis, Mo., J. Robens (ed.), USDA-ARS, Beltsville, Md. 20705, 1994; Chlan, C. et al., *Transformation and Regeneration of Cotton to Yield Improved Resistance to A. flavus* p. 15, Proceedings from the 7th Annual Aflatoxin Elim Workshop Meeting, St. Louis, Mo., J. Robens (ed.), USDA-ARS, Beltsville, Md. 20705, 1994; Dandekar, A. et al., *Process in engineering walnuts for resistance to Aspergillus flavus*, p. 18, Proceedings from the 7th Annual Aflatoxin Elim Workshop Meeting, St. Louis, Mo., J. Robens (ed.), USDA-ARS, Beltsville, Md. 20705, 1994; Li, Z. et al., *Development of Gene Delivery Systems Capable of Introducing Aspergillus flavus-Resistance Genes into Peanuts* p. 12, Proceedings from the 7th Annual Aflatoxin Elim Workshop Meeting, St. Louis, Mo., J. Robens (ed.), USDA-ARS, Beltsville, Md. 20705, 1994; Ozias-Akins, P. et al., *Genetic Engineering of Peanut-Insertion of Four Genes that May Offer Disease Resistance Strategies,* p. 14, Proceedings from the 7th Annual Aflatoxin Elim Workshop Meeting, St. Louis, Mo., J. Robens (ed.), USDA-ARS, Beltsville, Md. 20705, 1994; Weissinger, A. et al., *Progress in the Development of Transgenic Peanut with Enhanced Resistance to Fungi,* p. 13, Proceedings from the 7th Annual Aflatoxin Elim Workshop Meeting, St. Louis, Mo., J. Robens (ed.), USDA-ARS, Beltsville, Md. 20705, 1994. Unfortunately, no finding has yet been made that such antifungal agents function as a defense against the toxicity caused by Aspergillus spp.

As a second approach, attempts have been made to control aflatoxin/sterigmatocysin production through the use of biocontrol agents. For example, studies have focussed on atoxigenic Aspergillus isolates to compete with toxigenic isolates. These have not yet succeeded in halting aflatoxin/sterigmatocystin contamination. Unsuccessful attempts have further been made on methods of promoting competitive microorganisms in the soil.

A third approach has been to identify those endogenous "anti-aflatoxin/Aspergillus" molecules in aflatoxin-free plants which have been demonstrated physiologically to function in vivo against Aspergillus spp. or which suppress the production of aflatoxin. A suggested model useful for the identification of such molecules is soybean (*Glycine max* L.), a leguminous species that produces oil rich seeds and which is virtually immune to Aspergillus invasion and subsequent aflatoxin contamination. Howell, R. W., *Mycotoxin in Research in Oil Seeds*, pp. 61–66, Proc. 1st US-Japan Conference on Toxic Microorg., U.S. Department of Interior and UJNR Panels on Toxic Micro-Organisms, Washington, DC; Martinson, C. A. et al., *Detecting Corn Germplasm with Resistance to Aflatoxin Production in Kernel Extracts*, p. 8, Proceedings from the 7th Annual Aflatoxin Elim Workshop Meeting, St. Louis, Mo., J. Robens (ed.), USDA-ARS, Beltsville, Md. 20705, 1994. Further, it has been suggested that the lipoxygenase pathway produces antifungal compounds that could be involved in keeping soybean free of aflatoxin contamination. Such compounds include the volatile $C_6$ aldehydes hexanal or cis-3-hexenal (which isomerizes into trans-2-hexenal) from the 13-hydroperoxides of linoleic and linolenic acid by hydroperoxide lyases. See Doehlert D.C. et al., *Evidence Implicating Lipoxygenase Pathway in Providing Resistance to Soybeans Against Aspergillus flavus*, 83:1473–1477, Phytopathology, 1993.

Other diversified studies have focused on the identification of a single gene product to transfer to susceptible crops which can inhibit Aspergillus growth and/or aflatoxin/sterigmatocystin biosynthesis. Some research endeavors have centered on transforming foreign genes into susceptible aflatoxin/sterigmatocystin crops. To date, such genes have not resulted in reducing or eliminating either aflatoxin or sterigmatocysin contamination.

SUMMARY OF THE INVENTION

The invention relates to a novel method of inhibiting the production of mycotoxins of fungi such as aflatoxin and sterigmatocystin producing fungus in plants susceptible to contamination by such mycotoxins. Suitable plants include peanuts, cotton, tree nuts, corn, rice and walnuts. The process comprises introducing into such susceptible plants a gene encoding for an enzyme within the lipoxygenase pathway. The enzyme is one which partakes in the generation of a mycotoxin-inhibiting agent. Such agents include the 13-hydroperoxide reaction products of such lipoxygenases as soybean lipoxygenase. Along with soybean lipoxygenase, other suitable enzymes within the lipoxygenase pathway especially suited for use in the invention are those enzymes, such as the allene oxidases and hydroperoxide lyases. In a preferred embodiment, the 13-hydroperoxide reaction products are 13-hydroperoxy linoleic acid and 13-hydroperoxy linolenic acid.

The invention further comprises inactivating or altering the lipoxygenase used in the production of the 9-hydroperoxide reaction products, such as 9-hydroperoxy linoleic acid and 9-hydroxyperoxy linolenic acid, and derivatives thereof through the creation of antisense and other suitable constructs. Still further, the invention comprises a method of preparing a plant resistant to mycotoxins of fungi by mutating a gene which encodes for the mycotoxin inducing enzyme in the lipoxygenase pathway.

The invention is further drawn to a transgenic plant substantially resistant to mycotoxin contamination. The transgenic plant is prepared by incorporating into a pliant susceptible to such contamination a gene encoding for an enzyme within the lipoxygenase pathway—the enzyme being one involved in the generation of the mycotoxin-inhibition agent. Alternatively, transgenic plants are obtained by incorporating into the plant susceptible to such contamination replication antisense genes for any 9-hydroperoxide producing lipoxygenase or lipoxygenase pathway enzyme which produces an aflatoxin-sterigmatocystin inducing product. Still further, the invention relates to transgenic plants which result from mutation of the gene which encodes for the aflatoxin- or sterigmatocystin-inducing enzyme in the lipoxygenase pathway.

DETAILED DESCRIPTION OF THE INVENTION

The production of aflatoxin is influenced by high levels of oxidized fatty acids such as fatty acid hydroperoxides. Fatty acid hydroperoxides can be formed enzymatically by lipoxygenases. Lipoxygenases are plant enzymes which catalyze the addition of molecular oxygen to unsaturated fatty acids containing cis, cis-1,4-pentadiene moieties. The resulting hydroperoxide products contain a set of cis, trans-double bonds.

While many polyunsaturated fatty acids or fatty acid-containing molecules may serve as lipoxygenase substrates, the major substrate of lipoxygenase in plant seeds is linoleic acid. Since oxygen can add to either end of the pentadiene system, the major hydroperoxides of linoleic acid are 9-hydroperoxy linoleic acid (9-HPODE) and 13-hydroperoxy linoleic acid (13-HPODE).

Linolenic acid, the second major lipoxygenase substrate in plants, produces 9-hydroperoxy linolenic acid (9-HPOTE) and 13-hydroperoxy linolenic acid (13-HPOTE).

Degradation of such hydroperoxides in later steps within the lipoxygenase pathway leads to multiple byproducts, depending on the substrate, the specificity of the lipoxygenase and the activities of enzymes catalyzing the subsequent steps. Hexanal, trans-2-hexenal and trans-2-nonenal—hydroperoxide metabolites produced in the presence of hydroperoxide lyase—have been reported to inhibit aflatoxin production. See, for instance, Zeringue et al, *Aflatoxin Production in Cultures of Aspergillus flavus Incubated in Atmospheres Containing Selected Cotton Leaf-Derived Volatiles*, 28:445–448, 1990.

Another metabolite known to inhibit aflatoxin production is jasmonic acid and esters thereof, such as methyl jasmonate. This is a metabolite of 13-hydroperoxy linolenic acid produced in the presence of hydroperoxide dehydratase. Jasmonic acid and its derivatives are endogenous plant growth regulators.

The invention is drawn to a method of inhibiting or suppressing the effects of mycotoxins, such as aflatoxin and sterigmatocystin, by introducing into a crop susceptible to such mycotoxin contamination, a gene encoding for an enzyme within the lipoxygenase pathway; the enzyme being one which partakes in the generation of the mycotoxin-inhibiting agent. Mycotoxin-inhibiting agents include lipoxygenase, the allene oxidases, hydroperoxide dehydratase and hydroperoxide lyase. Particularly preferred lipoxygenases are soybean lipoxygenase 1 and Arabidopsis lipoxygenase. Promoters may be fused to the lipoxygenase genes by methods well known in the art. See, for example, Bell, E. et al., *Lipoxygenase Gene Expression is Modulated in Plants by Water Deficit, Wounding and Methyl Jasmonate*, Mol Gen Genet 230:456–462, 1991. Mycotoxin-inhibiting agents include the 13-hydroperoxides, decomposition products of the 13-hydroperoxides such as trans-2-hexenal and trans-2-nonenal as well as precursors to the 13-hydroperoxides.

Soybean is one of the few species with lipid rich seeds that is free of aflatoxin contamination. Soybean contains at least three lipoxygenases. The products of soybean lipoxygenase 1 (e.g. 13-HPODE and 13-HPOTE) in turn inhibit the accumulation of norsolorinic acid, an early intermediate in the aflatoxin pathway. Soybean lipoxygenase 1 produces almost exclusively the 13-hydroperoxy products. Soybean lipoxygenase 2 and 3, on the other hand, produce equal amounts of the 9- and 13- hydroperoxy products. The introduction of the gene encoding for soybean lipoxygenase 1 renders the most favorable results in the invention. 9-HPODE and 9-HPOTE were observed to induce mycotoxin production in aflatoxin and sterigmatocystin producing fungi.

The type of reaction product of lipoxygenase varies and is dependent upon the lipoxygenase 3-dimensional shape. While soybean seeds contain as its predominant lipoxygenase product 13-HPODE and a minor amount of 13-HPOTE, other aflatoxin susceptible crops, such as corn seed, produce primarily 9-HPODE and a minor amount of 9-HPOTE.

In accordance with the invention, any lipoxygenase, hydroperoxide lyase, allene oxidase and other lipoxygenase pathway genes are introduced into an aflatoxin/sterigmatocystin susceptible plant under the control of either an inducible plant promoter or a constitutive plant promoter. It is preferred to place the lipoxygenase pathway genes under an inducible promoter which is turned on only during fungal attack.

Suitable as the promoter are plant virus promoters, such as the cauliflower mosaic 35s (constitutive) promoter as well as other seed specific promoters such as the vegetative storage protein vsg (inducible) promoter from Arabidopsis. Such constructs are then transformed into the plant susceptible to contamination of Aspergillus spp. using established techniques. See, for instance, Nunberg, A. M. et al., *Development and Hormonal Regulation of Sunflower Helianthinin Genes: Proximal Promoter Sequences Confer Regionalized Seed Expression.* 6:473–486, The Plant Cell, 1994.

In a particularly preferred embodiment of the invention, 13-HPOTE is used to inhibit or retard the production of aflatoxin as well as decrease and delay aflatoxin gene expression and decrease growth of Aspergillus spp. Especially desirable effects of 13-HPOTE have been observed in delaying aflatoxin gene expression (ver-1) and in decreasing growth of *Aspergillus parasiticus.*

In another particularly preferred embodiment of the invention, 13-HPODE is used to decrease production of aflatoxin as well as sterigmatocystin, decrease and delay aflatoxin and sterigmatocystin gene expression (observed in ver-1 and stcU, respectively) and decrease growth of *Aspergillus parasiticus* and *Aspergillus nidulans.* In fact, reduction in the production of both aflatoxin and sterigmatocystin occurs even at low concentrations, such as 1 μm.

The invention further recognizes the ability of 9-HPODE and 9-HPOTE to induce mycotoxin production in aflatoxin and sterigmatocystin producing seed crops. In particular, 9-HPODE was particularly found to be effective in prolonging aflatoxin and sterigmatocystin gene expression (observed in ver-1 and stcU, respectively). [9-HPODE was seen not to decrease growth of *A. parasiticus.* Nor does it decrease or delay aflatoxin or sterigmatocystin gene expression (ver-1 and stcU, respectively).]

The mechanism by which 13-HPODE and 13-HPOTE inhibit the aflatoxin/sterigmatocystin pathway is believed to occur by directly (i) interfering with Aspergillus growth and/or (ii) interfering with aflatoxin/sterigmatocystin regulatory genes and/or (iii) repressing aflatoxin/sterigmatocystin gene expression.

In contrast, 9-HPODE and 9-HPOTE is believed to boost aflatoxin/sterigmatocystin production by delaying the natural "turning off" of the genes in the pathway or by directly derepressing aflatoxin/sterigmatocystin gene expression by Aspergillus. The mechanism by which mycotoxin production is controlled in one strain is believed to control mycotoxin production in another strain. For example, aflatoxin/sterigmatocystin production in *A. flavus, A. parasiticus* and *A. nidulans* is believed to be regulated very similarly.

The present invention further involves the genetic transformation of plants to include lipoxygenase for the protection of aflatoxin/sterigmatocystin contamination in susceptible host crops through typical plant transformation techniques. Aflatoxin/sterigmatocystin susceptible crops may be transformed with lipoxygenases which predominately produce 13-HPODE such as soybean lipoxygenase 1 or Arabidopsis lipoxygenase or other suitable lipoxygenases by techniques well established in the art. See, for example, Bell, E. et al., *Lipoxgenase Gene Expression is Modulated in Plants by Water Deficit, Wounding and Methyl Jasmonate,* Mol Gen Genet 230:456–462, 1)1991, as well as Cary, J. W. et al., *Construction of Transformation Vectors Expressing Resistance to A. flavus in Cotton,* p. 16, Proceedings from the 7th Annual Aflatoxin Elim Workshop Meeting, St. Louis, Mo., J. Robens (ed.), USDA-ARS, Beltsville, Md. 20705, 1994; Chlan, C. et al., *Transformation and Regeneration of Cotton to Yield Improved Resistance to A. flavus,* p. 15, Proceedings from the 7th Annual Aflatoxin Elim Workshop Meeting, St. Louis, Mo., J. Robens (ed.), USDA-ARS, Beltsville, Md. 20705, 1994; Dandekar, A. et al., *Process in engineering walnuts for resistance to Aspergillus flavus* p. 18, Proceedings from the 7th Annual Aflatoxin Elim Workshop Meeting St. Louis, Mo., J. Robens (ed.), USDA-ARS, Beltsville, Md. 20705, 1994; Li, Z. et al., *Development of Gene Delivery Systems Capable of Introducing Aspergillus flavus-Resistance Genes into Peanuts,* p. 12, Proceedings from the 7th Annual Aflatoxin Elim Workshop Meeting, St. Louis, Mo., J. Robens (ed.), USDA-ARS, Beltsville, Md. 20705, 1994; Ozias-Akins, P. et al., *Genetic Engineering of Peanut-Insertion of Four Genes that May Offer Disease Resistance Strategies,* p. 14, Proceedings from the 7th Annual Aflatoxin Elim Workshop Meeting, St. Louis, Mo., J. Robens (ed.), USDA-ARS, Beltsville, Md. 20705, 1994; Weissinger, A. et al., *Progress in the Development of Transgenic Peanut with Enhanced Resistance to Fungi,* p. 13, Proceedings from the 7th Annual Aflatoxin Elim Workshop Meeting, St. Louis, Mo., J. Robens (ed.), USDA-ARS, Beltsville, Md. 20705, 1994. Aflatoxin/sterigmatocystin susceptible crops include peanuts, cotton, tree nuts, rice, almonds, Brazil nuts, pistachios, melon, pumpkin, sunflower seeds, walnuts and corn.

Unlike the solutions proposed in the prior art relating to aflatoxin/sterigmatocystin contamination of food crops, the possibility of adverse health effects on consumers is not an area of concern in this invention. This is so since the novel transgenic food crops recited herein involve the incorporation of lipoxygenase or another lipoxygenase pathway enzyme from an edible plant into another edible plant. Humans, as well as organisms, easily degrade these enzymes by digestion.

A preferred embodiment of the invention is the use of lipoxygenase as an "anti-Aspergillus aflatoxin/ sterigmatocystin" deterrent. This embodiment is especially preferred since it does not require further treatments to the susceptible crops; the susceptible crops developing their own defense mechanism after introduction of the 13-hydroperoxy producing lipoxygenase or the antisense gene to the 9-hydroperoxy producing lipoxygenase.

Since corn seed lipoxygenase produces only exclusively the 9-hydroperoxy products, corn seed lipoxygenase is especially preferred in this embodiment. Such 9-HPODE and 9-HPOTE serve to prolong the expression of genes in the sterigmatocystin/aflatoxin pathway. In a preferred embodiment of this invention, an antisense gene to native 9-HPODE or 9-HPOTE producing lipoxygenases is introduced to aflatoxin/sterigmatocystin susceptible crops in order to reduce the production of the mycotoxin. A similar strategy can be taken for other lipoxygenase pathway genes, such as corn allene oxide, which generate products which prolong aflatoxin/sterigmatocystin gene expression. An antisense allene oxide gene is exemplary which can be introduced into corn.

Another preferred embodiment of the invention relates to a plant resulting from mutagenesis wherein the gene encoding for aflatoxin- or sterigmatocystin-inducing enzyme in the lipoxygenase pathway is mutated to a sufficient degree such that production of aflatoxin or sterigmatocystin is inhibited. Particularly desirable results have been obtained by mutating 9-HPODE and 9-HPOTE producing lipoxygenases until such lipoxygenases are non-functional. The gene is mutated by techniques such as by UV radiation or chemical mutagens.

The only analysis necessary for lipoxygenase (and antisense and mutant lipoxygenase) transformed crops is the determination as to whether the lipoxygenase from the foreign or transformed organism modifies the lipid content of the transformed plant seed in an undesirable manner. However, since biosynthesis of the major fatty acids is relatively unaffected by the presence of lipoxygenase, typically there is little, if any, change in the lipid composition of the host crop. Should there be an unacceptable change seen in the lipid composition, variations in the level of lipoxygenase expression easily ameliorates any undesirable effects.

The following examples will illustrate the practice of the present invention in its preferred embodiments. Other embodiments within the scope of the claims herein will be apparent to one skilled in the art from consideration of the specification and practice of the invention as disclosed herein. It is intended that the specification, together with the examples, be considered exemplary only, with the scope and spirit of the invention being indicated by the claims which follow.

EXAMPLES

Aflatoxin, sterigmatocystin, soybean lipoxygenase 1, (LOX1), linoleic and linolenic acid and all other chemicals unless otherwise specified were obtained from Sigma Chemical Company (St. Louis, Mo.).

Medium 1 (A&M, an aflatoxin inducing medium) for growing *A. parasiticus.*

| | Amount |
|---|---|
| Component | |
| Sucrose | 50 g |
| Ammonium Sulfate | 3 g |
| Potassium Phosphate (monobasic) | 10 g |
| Magnesium Sulfate | 2 g |
| Micronutrient solution* | 1 ml |
| Double distilled water | to a volume of 1000 ml |
| *Micronutrient Solution | |
| Composition | |
| $NaB_4O_7 \cdot 10H_2O$ | 0.7 g |
| $(NH_4)_6Mo_7O_{24} \cdot 4H_2O$ | 0.5 g |
| $Fe_2(SO_4)_3 \cdot 6H_2O$ | 10.0 g |
| $CuSO_4 \cdot 5H_2O$ | 0.3 g |
| $MnSO_4 \cdot H_2O$ | 0.11 g |
| $ZnSO_47H_2O$ | 17.6 g |
| Double distilled water | to a volume of 100 ml |

Medium 2, *A. nidulans* medium with either ammonium ditartarate or nitrate as the nitrogen source. Ammonium induces sterigmatocystin production to higher levels than nitrate.

| | Amount Needed |
|---|---|
| Composition | |
| 20 × Salts* (with ammonium ditartarate) | 50 ml |
| Trace elements** | 1 g |
| D-glucose (dextrose) | 20 g |
| Peptone | 2 g |
| Yeast Extract | 1 g |
| Casein amino acids (Casein hydrolysate) | 1 g |
| Double distilled water | to 1000 ml |
| The growth media for growing *A. nidulans* in nitrate was as follows: | |
| 20 × Salts* (with sodium nitrate) | 50 ml |
| Trace elements** | 1 ml |
| D-glucose (dextrose) | 20 g |
| Peptone | 2 g |
| Yeast extract | 1 g |
| Casein amino acids (Casein hydrolysate) | 1 g |
| Double distilled water | to 1000 ml |
| *20X Salts [with (i) ammonium ditartarate or (ii) sodium nitrate] | |
| Composition | |
| (i) ammonium ditartarte/(ii) sodium nitrate | (i)40.0 g/(ii)120.0/g |
| KCl | 10.4 g |
| $MgSO_4 \cdot 7H_2O$ | 10.4 g |
| $KH_2PO_4$ | 30.4 g |
| Double distilled water | to 1000 ml |
| **Trace Elements | |
| $ZnSO_4 \cdot 7H_2O$ | 2.20 g |
| $H_3BO_3$ | 1.10 g |
| $MnCl_2 \cdot 4H_2O$ | 0.50 g |
| $FeSO_4 \cdot 7H_2O$ | 0.50 g |
| $CoCl_2 \cdot 5H_2O$ | 0.16 g |
| $CuSO_4 \cdot 5H_2O$ | 0.16 g |
| $(NH_4)_6Mo_7O_{24} \cdot 4H_2O$ | 0.11 g |
| $Na_4EDTA$ | 5.00 g |

Medium 3 (PMS, an aflatoxin repressing medium)

| Composition | Amount Needed |
|---|---|
| Peptone | 50 g |
| Ammonium Sulfate | 3 g |
| Potassium Phosphate (monobasic) | 10 g |

| Composition | Amount Needed |
|---|---|
| Magnesium Sulfate | 2 g |
| Micronutrient solution* | 1 ml |
| Double distilled water | to a volume of 1000 ml |

*Same micronutrient solution set forth above

13-HPODE and 13-HPOTE were synthesized by combining linoleic (for 13-HPODE) or linolenic acid (for 13-HPOTE) with soybean lipoxygenase 1. Specifically, 3 mM appropriate fatty acid was mixed with 0.09% TWEEN® 20, 50 mM of potassium borate buffer, 0.2 mg/ml of lipoxygenase. The reaction mixture was adjusted to pH 10 with KOH and subjected to oxygenation by bubbling pure oxygen through the mixture for 20 min at 21° C. at which time the mixture was adjusted to pH 4 with 5M HCl and extracted with 2:1 (v/v) $CHCl_3:CH_3OH$. The reaction products (13-HPODE from linoleic acid and 13-HPOTE from linolenic acid) in $CHCl_3$ were fractionated and purified on a SilicAR CC-4 column and purity of the product obtained was verified with reverse phase HPLC.

The 9-HPODE was prepared from a crude extract of tomato fruit (~250 g). Specifically, ripe tomatoes were peeled, seeds discarded, and the pulp homogenized for 1 min in 150 ml of cold 0.5M NaOAc buffer (pH 5.5) and 2 mM ammonium linoleate. (The ammonium linoleate was made by adding 2 mM of linoleic acid to 1N ammonium hydroxide.) The mixture was then homogenized and incubated 40 min at 25° C. Oxygen was bubbled through and the mixture was extracted as described for the synthesis of 13-HPODE/13-EPOTE above. All three hydroperoxy products (13-HPOTE, 13-BPODE and 9-HPODE) were prepared as solutions in methanol.

EXAMPLE 1

This example illustrates the antifungal activity against Aspergillus spp. and the ability to inhibit aflatoxin/sterigmatocystin production.

*Aspergillus parasiticus* strain SK1, ATCC 98106, is a white-spored aflatoxin mutant that accumulates visible quantities of the pigment norsolorinic acid. Norsolorinic acid is the first stable intermediate in the aflatoxin/sterigmatocystin biosynthetic pathway and thus must be produced prior to formation of aflatoxin/sterigmatocystin. Norsolorinic acid and aflatoxin are produced under the same conditions both in vitro and in vivo for Aspergillus isolates. The *Aspergillus parasiticus* strain ATCC 98106 enables dual assessment of both norsolorinic acid and aflatoxin production.

*Aspergillus parasiticus* ATCC 98106 was grown in growth Medium 1 (Control - Condition A) containing soybean lipoxygenase 1 and linoleic acid (Condition B) and in a growth media containing only soybean lipoxygenase 1 (Condition C) and in a growth media containing only linoleic acid (Condition D). Linoleic acid was added in 100 µM amounts and lipoxygenase as 0.04 mg/ml of Medium 1.

The amount of visible norsolorinic acid in each sample is set forth in Table I.

TABLE I

| Treatment | Norsolorinic Acid Concentration After 24 Hours | Norsolorinic Acid Concentration After 48 Hours |
|---|---|---|
| Condition A | ++ | +++ |
| Condition B | − | − |
| Condition C | ++ | +++ |
| Condition D | ++ | +++ |

− = No Norsolorinic Acid
+ = Slight
++ = Much
+++ = Greatest

The results set forth in Table I illustrate that norsolorinic acid and hence aflatoxin biosynthesis were inhibited in *Aspergillus parasiticus* ATCC 98106 when the fungus was grown in media containing soybean lipoxygenase 1 plus linoleic acid but not in media with lipoxygenase or linoleic acid alone. This demonstrates therefore that 13-HPODE, the direct product of soybean lipoxygenase 1 and linoleic acid, or its derivatives is the compound responsible for the inhibition of aflatoxin and sterigmatocystin. This fact is further borne out by the results for Condition F below in Table II.

In Condition F, 100 micromoles of 13-HPODE dissolved in 75 ul of methanol was directly added to the growth media. Production of norsolorinic acid was visibly delayed for 24 hours. Organic extracts of the culture filtrate showed no production of aflatoxin. The results are presented in Table II below. (Condition E is growth media plus 75 ul methanol only.)

TABLE II

| Treatment | Aflatoxin Concentration After 24 Hours (ppb) | Aflatoxin Concentration After 48 Hours |
|---|---|---|
| Condition E | 88.79 | 140.79 |
| Condition F | 0 | 0 |

EXAMPLE 2

This example illustrates the effects of hydroperoxy fatty acids on Aspergillus growth.

Fungal isolates used in this study were the sterigmatocystin producing *A. nidulans* FGSC26 (Fungal Genetics Stock Center, Department of Microbiology, University of Kansas Medical Center, Kansas City, Kans.) and *A. parasiticus* ATCC 98106 as described in Example 1. Isolates were maintained as silica (room temperature) or glycerol (~80° C.) stocks. *A. parasiticus* was grown at 30° C. on potato dextrose agar and *A. nidulans* at 37° C. on Aspergillus minimal medium agar (as previously described) for conidial spore production. Conidia were harvested in TWEEN® 20 (0.1%), water and adjusted to desired inoculum concentration ($1 \times 10^6$ conidia/ml).

13-HPODE and 13-HPOTE were synthesized by combining linoleic (for 13-HPODE) or linolenic acid (for 13-HPOTE) with soybean lipoxygenase. Specifically, 5.4 mM appropriate fatty acid was mixed with 0.09% TWEEN® 20, 5.0 mM borate and 0.04 mg lipoxygenase/ml. The reaction mixture was adjusted to pH 10 with KOH and subjected to oxygenation by bubbling pure oxygen through the mixture for 40 min. at 21° C. at which time the mixture was adjusted to pH 4 with HCl and extracted with 2:1 (v/v) $CHCl_3:CH_3OH$. The reaction products (13-HPODE and 13-HPOTE) in $CHCl_3$ were fractionated and purified on a SilicAR CC-4 column and purity of the product obtained was verified with reverse phase HPLC.

The 9-HPODE was prepared from a crude extract of tomato fruit (~250 g). Specifically, ripe tomatoes were sliced and mixed with 0.1M NaOAc buffer (pH 5.5) and ammonium linoleate (1 mM). The mixture was then homogenized and incubated ~20 min. at 25° C. Oxygen was bubbled through and the mixture was extracted as described for the synthesis of 13-HPODE/13-HPOTE above. All three hydroperoxy products (13-HPOTE, 13-HPODE and 9-HPODE) were prepared as solutions in methanol.

Mycelial cultures of A. parasiticus were grown for 36 h at 250 rpm at 30° C. in 500 ml of Medium 3. Mycelia were harvested by suction filtration through cheesecloth and equal fresh weights of mycelia (~400 mg wet weight) were then transferred into 40 ml of Medium 1 containing the same amount of methanol as the hydroperoxy treatments (~0.1%). Treatments were 1, 10 or 100 $\mu$M of 13-HPODE, 13-HPOTE or 9- PODE and a control (Medium 1 only). Mycelium and extracts were harvested 12, 24, 48, 72 or 96 h after transfer. All time points were replicated 4 times. Lyophilized mycelial weight was obtained from 3 treatments for effects on growth, filtrate from one or 3 combined flasks was analyzed for aflatoxin production (Example 4), and mycelia from the fourth treatment was saved for MRNA analysis (Example 3).

A. nidulans mycelial culture was started by inoculating complete nitrate medium with 1×10$^6$ spores/ml and growing the culture at 300 rpm, 37° C., for 12 h. Using the same procedure as described above, mycelia was transferred to 40 ml of the sterigmatocystin inducing medium, complete ammonium ditartarate media. Treatments were 1, 10 or 100 $\mu$M of 13-HPODE or 9-HPODE and a control. Subsequent procedures used were similar to those applied to A. parasiticus recited above.

The effects of different concentrations of 13-HPODE, 13-HPOTE or 9-HPODE on growth (e.g. mycelial dry weight) of Aspergillus spp. are shown in Tables III–VI. The data shows that 13-HPODE and 13-HPOTE inhibit fungal growth whereas 9-HPODE has no effect on A. parasiticus growth.

TABLE III

Aspergillus parasiticus strain ATCC 98106

| Treatment | Mean Dry Weight (in mg) of mycelium at different time (h) after transfer | | |
|---|---|---|---|
| | 12h | 24h | 48h |
| Control | 3.60 | 5.00 | 5.23 |
| +1$\mu$M 13-HPODE | 2.63 | 4.30 | 4.72 |
| +10$\mu$M 13-HPODE | 2.63 | 4.24 | 4.70 |
| +100$\mu$M 13-HPODE | 2.17 | 4.13 | 4.76 |

TABLE IV

Aspergillus nidulans FGSC 26.

| Treatment | Mean Dry Wt (in mg) at different time (h) after transfer | | |
|---|---|---|---|
| | 12h | 24h | 48h |
| Control | 3.33 | 6.67 | 12.50 |
| +1$\mu$M 13-HPODE | 3.53 | 5.73 | 12.00 |
| +10$\mu$M 13-HPODE | 2.80 | 4.23 | 11.40 |
| +100$\mu$M 13-HPODE | 2.20 | 3.80 | 11.00 |

TABLE V

Aspergillus parasiticus strain ATCC 98106

| Treatment | Mean Dry Wt (in mg) at different time (h) after transfer | | |
|---|---|---|---|
| | 12h | 24h | 48h |
| Control | 3.62 | 5.05 | 5.42 |
| +1$\mu$M 13-HPOTE | 2.89 | 4.38 | 4.75 |
| +10$\mu$M 13-HPOTE | 2.73 | 4.21 | 4.59 |
| +100$\mu$M 13-HPOTh | 2.37 | 4.14 | 4.20 |

TABLE VI

Aspelgillus parasiticus strain ATCC98106

| Treatment | Mean Dry Wt (in mg) at different time (h) after transfer | | |
|---|---|---|---|
| | 12h | 24h | 48h |
| Control | 3.65 | 5.38 | 5.79 |
| +1$\mu$M 9-HPODE | 3.68 | 5.00 | 5.69 |
| +10$\mu$M 9-HPODE | 3.56 | 5.17 | 5.65 |
| +100$\mu$M 9-HPODE | 3.60 | 5.08 | 5.73 |

13-hydroperoxy linoleic acid and 13-hydroperoxy linolenic acid applied at concentrations of 100 $\mu$m significantly decreased fungal growth at the 0.05 level of significance. The reduction trend was still apparent for at low concentrations at 1 $\mu$M and 10 $\mu$M. In contrast, 9-HPODE had no effect on A. parasiticus growth.

EXAMPLE 3

This example illustrates the effects of hydroperoxy fatty acids on Aspergillus aflatoxin and sterigmatocystin gene expression.

Mycelium from the experiment described in Example 2 was extracted for RNA analysis. Mycelium was harvested by suction filtration through cheesecloth, quickly frozen in liquid nitrogen and lyophilized. Mycelim was then ground up with a mortar and pestle and RNA extracted in Triazol (Gibco) as per the manufacturers specifications. Equal amount (20 mg) of total RNA per sample was separated by electrophoresis in 1.2% denaturing formaldehyde agarose gel and then transferred to Hybond nylon membrane (Amersham Corp.) by capillary action.

Expression of ver-1 (a gene encoding a ketoreductase essential for aflatoxin production in A. parasiticus) was carried out by probing with pBSV2 which contains the middle portion of ver-1 from A. parasiticus. Expression of stcU, an analogous gene in A. nidulans was analyzed by probing with pRB3 which contains the middle portion of stcU from A. nidulans. Labeled probes for each gene were prepared by a random priming kit (Pharmacia or BRL or Promega) using [$^{32}$P]dCTP (Dupont).

pBSV2 was obtained by transforming the aflatoxin mutant strain A. parasiticus SRRC 164—Southern Regional Research Center, USDA-ARS, 1100 Robert E. Lee Blvd., New Orleans, La. 70179—(also available as ATCC 36537) with a genomic library of an aflatoxin wildtype A. parasiticus strain SRRC 143 (i.e. ATCC 56775). pBSV 2 is a plasmid which contains the part of the piece of DNA which returns the aflatoxin producing ability to A. parasiticus SRRC 164. Sequence analysis of the gene (called ver-1) located on this DNA showed it to be a keto-reductase necessary for aflatoxin production, Skory, C. D. et al.

Isolation and Characterization of a Gene From Aspergillus parasiticus Associated With the Conversion of Versicolorin A to Sterigmatocystin in Aflatoxin Biosynthesis, 58:3527–3537, Appl Environ Microbiol, 1992. stcU (formerly called verA) is the A. nidulans homolog of ver-1. stcU was found by probing an A. nidulans FGSC26 genomic library (available from the Fungal Genetics Stock Center in Kansas City), with ver-1, Keller, N. P. et al., Aspergillus nidulans verA is Required for Production of the Mycotoxin Sterigmatocystin, 60:1444–1450, Appl Environ Microbiol, 1994. The A. nidulans piece of DNA homologous to ver-1 contained the gene stcU which is necessary for sterigmatocystin production in A. nidulans. stcU (subcloned on pRB3) and ver-1 both encode functionally equivalent ketoreductases and can be exchanged for each other. These genes can be cloned as described above or obtained from Dr. Keller (the inventor) or pBSV2 from Dr. John Linz, Department of Food Science, Michigan State University, East Lansing, Mich. 48824.

The effects of 13-HPODE, 13-HPOTE and 9-HPODE on ver-1 and stcU gene expression are shown in Tables VII–X. As can be seen in these tables, both ver-1 and stcU expression were delayed and repressed by any concentration of 13-HPODE and 13-HPOTE (Tables VII and VIII). The 13-HPOTE effects appeared more pronounced than those of 13-HPODE on ver-1 expression. Conversely, ver-1 and stcU expression were not delayed but rather prolonged by any concentration of 9-HPODE (Tables IX and X).

TABLE VII

| Treatment | Conc. ($\mu$M) | ver-1 Transcript 24 hr | 48 hr | stcU Transcript 24 hr | 48 hr |
| --- | --- | --- | --- | --- | --- |
| 13 HPODE | 0 | +++ | +++ | +++ | +++ |
|  | 1$\mu$M | ++ | ++ | − | ++ |
|  | 10$\mu$M | + | + | − | + |
|  | 100$\mu$M | − | + | − | − |

− = no expression
+ = little expression
++ = substantial expression
+++ = high expression

TABLE VIII

| Treatment | Conc. ($\mu$M) | ver-1 Transcript 24 hr | 48 hr |
| --- | --- | --- | --- |
| 13 HPOTE | 0 | +++ | +++ |
|  | 1$\mu$M | + | ++ |
|  | 10$\mu$M | − | − |
|  | 100$\mu$M | − | − |

− = no expression
+ = little expression
++ = substantial expression
+++ = high expression

TABLE IX

| Treatment | Conc. ($\mu$M) | ver-1 Transcript 24 hr | 48 hr | 72 hr | 96 hr |
| --- | --- | --- | --- | --- | --- |
| 9 HPODE | 0 | ++ | +++ | ++ | − |
|  | 1$\mu$M | ++ | +++ | +++ | ++ |
|  | 10$\mu$M | ++ | +++ | +++ | +++ |
|  | 100$\mu$M | ++ | +++ | +++ | +++ |

TABLE IX-continued

| Treatment | Conc. ($\mu$M) | ver-1 Transcript 24 hr | 48 hr | 72 hr | 96 hr |
| --- | --- | --- | --- | --- | --- |

− = no expression
+ = little expression
++ = substantial expression
+++ = high expression

TABLE X

| Treatment | Conc. ($\mu$M) | stcU Transcript 24 hr | 48 hr | 72 hr | 96 hr |
| --- | --- | --- | --- | --- | --- |
| 9 HPODE | 0 | ++ | +++ | ++ | + |
|  | 1$\mu$M | ++ | +++ | +++ | ++ |
|  | 10$\mu$M | ++ | +++ | +++ | +++ |
|  | 100$\mu$M | ++ | +++ | +++ | +++ |

− = no expression
+ = little expression
++ = substantial expression
+++ = high expression

EXAMPLE 4

This example illustrates the effects of hydroperoxy fatty acids on Aspergillus aflatoxin and sterigmatocystin.

Mycelium from the experiment described in Example 2 was extracted for sterigmatocystin analysis for A. nidulans and filtrate from the experiment described in Example 2 was extracted for aflatoxin analysis for A. parasiticus. For sterigmatocystin analysis, ~100 mg of lyophilized mycelia were crushed to fine powder using a spatula and resuspended in 10 ml of acetone:chloroform (1:1) for 30 minutes with gentle agitation. The resulting slurry was centrifuged at 5000 rpm for 10 minutes and the supernatant was collected and allowed to evaporate to dryness under the fume hood. The dried extract was reconstituted in 1 ml chloroform and injected in 20 ml aliquots into a Waters HPLC. ST was eluted from a C18 (5 mm) LiChroSorb Hibar column using a single solvent system (80% acetonitrile) at a flow rate of 1 ml/min. ST was detected at 245 nm.

For aflatoxin, 10 ml of filtrate was extracted 3 times with 20 ml acetone:chloroform (1:1) in a separatory funnel. The organic phase was collected, passaged over anhydrous sodium sulfate and allowed to evaporate to dryness under the fume hood. The dried extract was resuspended in 1 ml of chloroform. A 20 $\mu$l aliquot was injected into a Waters HPLC unit. Aflatoxin $B_1$ was eluted from a normal phase silica gel column using a single solvent system (750 ml chloroform, 225 ml cyclohexane, 25 ml isopropanol and 25 ml acetonitrile) at a flow rate of 2 ml/min. Aflatoxin was detected at 365 nm.

As can be seen in Tables XI and XII, all treatments of 13-HPODE and 13-HPOTE significantly reduced the amount aflatoxin and sterigmatocystin produced by Aspergillus parasiticus and A. nidulans respectively. On the other hand, 9-HPODE had no effect on aflatoxin production by A. parasiticus.

TABLE XI

| Treatment | Conc (μM) | Amount Aflatoxin (μg/mL) | | |
|---|---|---|---|---|
| | | 12 h | 24 h | 48 h |
| 13-HPODE | 0 | 0.35 | 0.70 | 2.09 |
| | 1 μM | 0.18 | 0.33 | 0.33 |
| | 10 μM | 0.03 | 0.15 | 0.20 |
| | 100 μM | 0.00 | 0.04 | 0.04 |
| 13-HPOTE | 0 | 0.27 | 0.45 | 0.68 |
| | 1 μM | 0.33 | 0.39 | 0.74 |
| | 10 μM | 0.00 | 0.48 | 0.78 |
| | 100 μM | 0.00 | 0.00 | 0.00 |
| 9-HPODE | 0 | 0.13 | 0.33 | 0.33 |
| | 1 μM | 0.09 | 0.22 | 0.19 |
| | 10 μM | 0.09 | 0.26 | 0.34 |
| | 100 μM | 0.03 | 0.28 | 0.51 |

TABLE XII

| Treatment | Conc (μM) | Time after shift | (ST (ng/mg-dry weight) | |
|---|---|---|---|---|
| | | | 24 h | 48 h |
| 13-HPODE | 0 | | 1.25 | 4.17 |
| | 1 μM | | 0.00 | 1.98 |
| | 10 μM | | 0.00 | 1.44 |
| | 100 μM | | 0.00 | 0.81 |

Combining the data from this example with the data from Examples 1, 2 and 3; it appears that 13-hydroperoxy fatty acids and/or their derivatives inhibit mycotoxin production by Aspergillus spp. whereas 9-hydroperoxy fatty acids and/or their derivatives prolong mycotoxin production by Aspergillus spp.

From the foregoing, it will be observed that numerous variations and modifications may be effected without departing from the true spirit and scope of the novel concepts of the invention.

What is claimed is:

1. A method of inhibiting the production of mycotoxins of fungi in plants susceptible to mycotoxin contamination which comprises stably transforming a crop susceptible to such contamination, and under the regulation of an operable promoter with a gene encoding for soybean lipoxygenase I, a lipoxygenase pathway enzyme for a mycotoxin-inhibiting agent, in an amount sufficient to inhibit production of mycotoxins.

2. The method of claim 1 wherein the mycotoxin is aflatoxin or sterigmatocystin.

3. The method of claim 1 wherein the soybean lipoxogenase I produces 13-hydroperoxy compounds selected from the group consisting of 13-hydroperoxy linolenic acid and 13-hydroperoxy linoleic acid.

4. The method of claim 1 wherein the fungus is an aflatoxin or sterigmatocystin producing fungus.

5. A plant which is substantially resistant to mycotoxin contamination of fungi which is obtained by stably transforming a plant susceptible to such contamination a gene encoding for soybean lipoxygenase I, a lipoxygenase pathway enzyme for a mycotoxin-inhibiting agent.

6. The plant of claim 5 wherein the fungi is any aflatoxin or sterigmatocystin producing fungus.

7. The method of claim 5 wherein the mycotoxin-inhibiting agent is selected from the group consisting of 13-hydroperoxy linolenic acid, and 13-hydroperoxy linoleic acid.

8. The plant of claim 5 wherein said plant susceptible to mycotoxin contamination is selected from the group consisting of peanuts, walnuts, cotton, tree nuts, almonds, Brazil nuts, pistachios, melon, pumpkin, sunflower seeds, maize and rice.

9. A method of inhibiting the toxicity in seed crops caused by aflatoxin-producing or sterigmatocystin-producing fungus which comprises stably transforming a crop susceptible to such contamination, and under the regulation of an operable promoter, a gene encoding for soybean lipoxygenase 1 in an amount sufficient to inhibit production of aflatoxin or sterigmatocystin.

* * * * *